United States Patent
Cong et al.

(10) Patent No.: US 10,561,167 B2
(45) Date of Patent: Feb. 18, 2020

(54) HYPOGLYCEMIC COMPOSITION AND PREPARATION METHOD THEREOF

(71) Applicant: INFINITUS (CHINA) COMPANY LTD, JiangMen (CN)

(72) Inventors: Renhuai Cong, JiangMen (CN); Fangli Ma, JiangMen (CN); Chung Wah Ma, JiangMen (CN)

(73) Assignee: INFINITUS (CHINA) COMPANY LTD., Jiang Men (CN)

( * ) Notice: Subject to any disclaimer, the term of this patent is extended or adjusted under 35 U.S.C. 154(b) by 355 days.

(21) Appl. No.: 15/534,640

(22) PCT Filed: Jan. 13, 2017

(86) PCT No.: PCT/CN2017/071109
§ 371 (c)(1),
(2) Date: Jun. 9, 2017

(87) PCT Pub. No.: WO2017/114515
PCT Pub. Date: Jul. 6, 2017

(65) Prior Publication Data
US 2018/0049459 A1  Feb. 22, 2018

(30) Foreign Application Priority Data
Dec. 30, 2015 (CN) .......................... 2015 1 1032106

(51) Int. Cl.
| | | |
|---|---|---|
| A61K 36/28 | (2006.01) | |
| A23L 33/105 | (2016.01) | |
| A61K 36/8962 | (2006.01) | |
| C11B 1/16 | (2006.01) | |
| A61K 36/23 | (2006.01) | |
| B01D 3/38 | (2006.01) | |

(52) U.S. Cl.
CPC ............ *A23L 33/105* (2016.08); *A61K 36/23* (2013.01); *A61K 36/8962* (2013.01); *B01D 3/38* (2013.01); *C11B 1/16* (2013.01); *A23V 2002/00* (2013.01); *A23V 2200/328* (2013.01)

(58) Field of Classification Search
CPC ...................................................... A61K 36/28
See application file for complete search history.

(56) References Cited

U.S. PATENT DOCUMENTS

2009/0186096 A1* 7/2009 Kritzman ............... C11D 3/505
424/523

FOREIGN PATENT DOCUMENTS

| CN | 1089152 | 7/1994 |
| CN | 103127437 | 6/2013 |
| JP | 4370309 | 11/2009 |

OTHER PUBLICATIONS

Google Patents English translation of Zhangqiu Baiyunhu Baimai Aquatic Products, CN 104719985 A, Jun. 2015 (Year: 2015).*
East, Bibliographic information for CN 104719985 A, Jun. 2015 (Year: 2015).*
Google Patents English translation of Jiangnan University and Zhejiang Oil Master Co. Ltd., CN 102524733 A, 2012 (Year: 2012).*
East, Bibliographic information for CN 102524733 A, 2012 (Year: 2012).*
Huang et al., "Protective Effect of FoeniculumVulgare Extract on Hepatic Injury of Early Stage in Diabetic Rats," *Chinese Journal of Experimental Traditional Medical Formulae*, 20(7): 181-184, 2014. (English abstract of Chinese publication).
Li et al., "Hypoglycemic Effect of Garlic Oil on Alloxan Diabetic Mice," *Food Science*, 31(23):344-348, 2010. (English abstract of Chinese publication).
PCT International Search Report issued in International Application No. PCT/CN2017/071109, dated Apr. 7, 2017. (English translation of Chinese text).
Sun, "Food Additives," Chemical Industry Press, pp. 63-64, 2008. (English abstract of Chinese publication).
Wang, "Storage and Transport of Garlic Bolt, Garlic Bulb and Onion," *Chinese Press of Agricultural Science and Technology*, p. 88, 2006. (English abstract of Chinese publication).
Zou et al., "264 Healthy Eating Habits Told by Diabetologists," Guizhou Science and Technology Publishing House, p. 159, 2015. (English abstract of Chinese publication).

* cited by examiner

*Primary Examiner* — Rosanne Kosson
(74) *Attorney, Agent, or Firm* — Parker Highlander PLLC

(57) ABSTRACT

The present invention provides a hypoglycemic composition and preparation method thereof, wherein the hypoglycemic composition comprises 1-99 parts by weight of anise oil and 1-99 parts by weight of onion oil. Compared with the prior art, the anise oil in the hypoglycemic composition of the present invention can inhibit aldose reductase and α-glucosidase. The active ingredients of onion oil are sulfonylurea butyric acid and volatile substances containing sulfur including alliin, allylpropyl disulfide, S-allylcysteine sulfoxide (SACS) and so on, which prevent insulin from being destroyed by oxidation-reduction equilibrium. Anise oil and onion oil act synergistically to facilitate the hypoglycemic effect; moreover, anise oil and onion oil can be both used as medicine and food, and have no side effect.

11 Claims, No Drawings

HYPOGLYCEMIC COMPOSITION AND PREPARATION METHOD THEREOF

CROSS REFERENCE TO RELATED APPLICATIONS

The present application is a National Phase entry of PCT Application No. PCT/CN2017/071109, filed on Jan. 13, 2017, which claims the priority of Chinese Patent Application No. 201511032106.0, as filed on Dec. 30, 2015 and titled with "A hypoglycemic composition and preparing method thereof", and the disclosure of which is incorporated herein by reference.

FIELD

The present invention belongs to the technical field of health food, particularly to a hypoglycemic composition and preparation method thereof.

BACKGROUND

Diabetes is a common chronic metabolic disease. With the continuous improvement of people's living standards, patients with diabetes are increasing. At present, China has more than 92 million of the patients with diabetes, and 100 million and 5 thousand persons are potential patients. As a multifactorial comprehensive disease, diabetes is difficult to cure, and patients need long-term medication, and complications of diabetes often lead to serious consequences. Diabetes is clinically manifested by hyperglycemia as the main characteristic; typical cases can have polyuria, polydipsia, polyphagia, weight loss and other symptoms, i.e. "three more, one less" symptoms. In addition to acute symptoms such as ketoacidosis, hypoglycemic coma, the complications of diabetes also comprise chronic complications mainly including vasculopathy and neuropathy. Vascular diseases mainly include foot disease, eye disease, heart disease and kidney disease, etc. Research shows that vasculopathy is mainly vascular scleratheroma lesion of corresponding organs. The direct cause of scleratheroma is excessive blood lipids.

At present, according to the different types of diabetes, the common treatment methods for patients with diabetes include insulin injection and oral hypoglycemic agents. Hypoglycemic agents mainly include biguanides and sulfonylureas, etc. The long-term use of these drugs is easy to produce drug resistance; the curative effect is more and more non-obvious over time and these drugs have lots of medication tabooes when taking as well as significant toxic side effects. For example, it has been shown that biguanides induce lactic acid acidosis, especially in diabetes patients with renal insufficiency, the mortality rate is 50%; sulfonylureas often leads to hypoglycaemic reaction in patients, etc.

Due to the low side effects, traditional Chinese medicine has been paid more and more attention in the medical field. However, since there are many kinds of formulations of traditional Chinese medicines and designed medicaments, it has been difficult to control the quality of the products. Therefore, the existing commonly used hypoglycemic drugs are mainly western medicines, such as rosiglitazone, which can achieve a better hypoglycemic effect.

SUMMARY

In view of this, the technical problem to be solved by the present invention is to provide a hypoglycemic composition having less side effects and preparation method thereof.

The present invention provides a hypoglycemic composition, comprising: 1-99 parts by weight of anise oil and 1-99 parts by weight of onion oil.

Preferably, the anise oil is obtained by subjecting anise to steam distillation; the onion oil is obtained by subjecting onion to steam distillation.

Preferably, 1-40 parts by weight of anise oil and 1-40 parts by weight of onion oil are included.

Preferably, 1-20 parts by weight of anise oil and 1-20 parts by weight of onion oil are included.

Preferably, 1-10 parts by weight of anise oil and 1-10 parts by weight of onion oil are included. 1111 The present invention further provides a method for preparing a hypoglycemic composition, comprising:

A) pulverizing anise and subjecting the resultant to steam distillation to obtain anise oil; pulverizing onion and subjecting the resultant to steam distillation to obtain onion oil;

B) mixing 1-99 parts by weight of anise oil and 1-99 parts by weight of onion oil to obtain the hypoglycemic composition.

Preferably, the step A) is performed by:
pulverizing anise, then soaking the resultant in water, and then subjecting the resultant to distillation by heating to obtain anise oil;
pulverizing onions, then soaking the resultant in water, and then subjecting the resultant to distillation by heating to obtain onion oil.

Preferably, after the anise is pulverized, the resultant is soaked in water for 10-30 h; after the onion is pulverized, the resultant is soaked in water for 10-30 h.

The present invention further provides use of a hypoglycemic composition for the preparation of a hypoglycemic medicament.

The present invention further provides use of a hypoglycemic composition for the preparation of a health food having the function of treating hyperglycemia.

The present invention provides a hypoglycemic composition and preparation method thereof, wherein the hypoglycemic composition comprises 1-99 parts by weight of anise oil and 1-99 parts by weight of onion oil. Compared with the prior art, the anise oil in the hypoglycemic composition of the present invention can inhibit aldose reductase and α-glucosidase. The active ingredients of onion oil are sulfonylurea butyric acid and volatile substances containing sulfur such as alliin, allylpropyl disulfide, S-allylcysteine sulfoxide (SACS) and so on, which prevent insulin from being destroyed by oxidation-reduction equilibrium. Anise oil and onion oil act synergistically to facilitate the hypoglycemic effect; moreover, anise oil and onion oil can be both used as medicine and food, and have no side effect.

DETAILED DESCRIPTION

The technical solutions of the Examples of the present invention are described clearly and completely hereinafter in connection with the Examples of the present invention. Obviously, the described Examples are only part of the Examples of the present invention, rather than all of them. Based on the Examples of the present invention, all of the other Examples obtained by those skilled in the art without exercising inventive efforts are within the protected scope of the present invention.

The present invention provides a hypoglycemic composition, comprising: 1-99 parts by weight of anise oil and 1-99 parts by weight of onion oil.

Among them, the present invention does not have special restriction on the origin of all raw materials, which can be sold on the market or self-prepared; the anise oil is preferably obtained by subjecting anise to steam distillation; the anise oil is preferably fennel oil; the onion oil is preferably obtained by subjecting onion to steam distillation.

In the hypoglycemic composition of the present invention, the content of the anise oil is preferably 1-60 parts by weight, more preferably 1-40 parts by weight, furthermore preferably 1-20 parts by weight, most preferably 1-10 parts by weight; in some Examples of the present invention, the anise oil is 10 parts by weight; in some Examples of the present invention, the anise oil is 5 parts by weight; in some other Examples of the present invention, the anise oil is 1 part by weight. Anise, which is warm and spicy, cold dispelling and pain relieving, regulating Qi and the medium warmer, has benefiting gallbladder, anti-ulcer and bactericidal effects, and can also prevent and treat diabetes by inhibiting aldose reductase and $\alpha$-glucosidase.

The content of the onion oil is preferably 1-60 parts by weight, more preferably 1-40 parts by weight, furthermore preferably 1-20 parts by weight, most preferably 1-10 parts by weight; in some Examples of the present invention, the onion oil is 1 part by weight; in some Examples of the present invention, the onion oil is 3 parts by weight; in some Examples of the present invention, the onion oil is 5 parts by weight; in some Examples of the present invention, the onion oil is 10 parts by weight; in some other Examples of the present invention, the onion oil is 20 parts by weight. Onion, which is warm, spicy and sweet, has expectorant, diuretic, stomachic and bowel moistening, detoxifying functions. The active ingredients of onion oil are sulfonylurea butyric acid and volatile substances containing sulfur such as alliin, allylpropyl disulfide, S-allylcysteine sulfoxide (SACS) and so on, which prevent insulin from being destroyed by oxidation-reduction equilibrium, thereby has hypoglycemic effect.

In some Examples of the present invention, the hypoglycemic composition comprises 10 parts by weight of anise oil and 1 part by weight of onion oil; in some Examples of the present invention, the hypoglycemic composition comprises 5 parts by weight of anise oil and 1 part by weight of onion oil; in some Examples of the present invention, the hypoglycemic composition comprises 1 part by weight of anise oil and 1 part by weight of onion oil; in some Examples of the present invention, the hypoglycemic composition comprises 1 part by weight of anise oil and 3 parts by weight of onion oil; in some Examples of the present invention, the hypoglycemic composition comprises 1 part by weight of anise oil and 5 parts by weight of onion oil; in some Examples of the present invention, the hypoglycemic composition comprises 1 part by weight of anise oil and 10 parts by weight of onion oil; in some Examples of the present invention, the hypoglycemic composition comprises 1 part by weight of anise oil and 20 parts by weight of onion oil.

In the hypoglycemic composition of the present invention, anise oil can inhibit aldose reductase and $\alpha$-glucosidase. The active ingredients of onion oil are sulfonylurea butyric acid and volatile substances containing sulfur such as alliin, allylpropyl disulfide, S-allylcysteine sulfoxide (SACS), which prevents insulin from being destroyed by oxidation-reduction equilibrium. The various fat ingredients in anise oil and onion oil act synergistically to produce better hypoglycemic effect; moreover, anise oil and onion oil can be both used as medicine and food, and have no side effect.

The present invention further provides a method for preparing the above-described hypoglycemic composition, comprising: A) pulverizing anise and subjecting the resultant to steam distillation to obtain anise oil; pulverizing onion and subjecting the resultant to steam distillation to obtain onion oil; B) mixing 1-99 parts by weight of anise oil and 1-99 parts by weight of onion oil to obtain the hypoglycemic composition.

Among them, methods well known by those skilled in the art can be used as the steam distillation without special restrictions. The present invention is preferably implemented by the following steps: pulverizing anise, then soaking the resultant in water, and then subjecting the resultant to distillation by heating to obtain anise oil; wherein the ratio between anise and water is preferably 1 g: (1-10) ml, more preferably 1 g: (3-7) ml, furthermore preferably 1 g: (4-6) ml; the soaking time is preferably 10-30 h, more preferably 15-30 h, furthermore preferably 20-30 h, most preferably 22-26 h; the distillation by heating is implemented until the distilled water contains no oil droplets.

Pulverizing onion, then soaking the resultant in water, and then subjecting the resultant to distillation by heating to obtain onion oil; wherein, the ratio of onion and water is preferably 1 g: (1-10) ml, more preferably 1 g: (3-7) ml, furthermore preferably 1 g: (4-6) ml; the soaking time is preferably 10-30 h, more preferably 15-30 h, furthermore preferably 20-30 h, most preferably 22-26 h; the distillation by heating is implemented until the distilled water contains no oil droplets.

Last, mixing 1-99 parts by weight of anise oil and 1-99 parts by weight of onion oil to obtain the hypoglycemic composition. The contents of anise oil and onion oil in the hypoglycemic composition are the same as above mentioned, so they are not repeated here.

The method of the present invention is simple and scientific, which can fully retain the fatty active ingredients of anise and onion. The reasonable combination of the above fatty ingredients ensure that the composition has hypoglycemic effect.

The present invention further provides use of the above mentioned hypoglycemic composition for the preparation of a hypoglycemic medicament; the hypoglycemic medicament further comprises pharmaceutically acceptable excipients; the hypoglycemic medicament can be formulated into many dosage forms such as granules, capsules, oral agents or syrups, etc.

The present invention further provides use of the above mentioned hypoglycemic composition for the preparation of a health food having the function of treating hyperglycemia; the health food can be formulated into many dosage forms such as granules, capsules, oral agents or syrups, which is preferably capsules, tablets, powder, granules, soft candies, emulsions or oral liquids.

To further illustrate the present invention, the hypoglycemic composition and preparation method thereof provided by the present invention are illustrated in details in connection with Examples hereinafter.

The reagents used in the following Examples are commercially available.

Example 1

After anise is pulverized, water was added at a ratio of anise powder and water of 1 g: 5 ml, then the mixture was placed into a steam distillation device, soaked for 24 h, subjected to distillation by heating until the distilled water contains no oil droplets. After a distillation time of 3 h, anise oil was obtained.

After onions are pulverized, water was added at a ratio of onion powder and water of 1 g: 5 ml, then the mixture was placed into a steam distillation device, soaked for 24 h, subjected to distillation by heating until the distilled water contains no oil droplets. After a distillation time of 3 h, onion oil was obtained.

10 parts by weight of anise oil and 1 part by weight of onion oil were mixed to obtain the hypoglycemic composition.

Example 2

5 parts by weight of the anise oil obtained in Example 1 and 1 part by weight of the onion oil obtained in Example 1 were mixed to obtain the hypoglycemic composition.

Example 3

1 part by weight of the anise oil obtained in Example 1 and 1 part by weight of the onion oil obtained in Example 1 were mixed to obtain the hypoglycemic composition.

Example 4

1 part by weight of the anise oil obtained in Example 1 and 3 parts by weight of the onion oil obtained in Example 1 were mixed to obtain the hypoglycemic composition.

Example 5

1 part by weight of the anise oil obtained in Example 1 and 5 parts by weight of the onion oil obtained in Example 1 were mixed to obtain the hypoglycemic composition.

Example 6

1 part by weight of the anise oil obtained in Example 1 and 10 parts by weight of the onion oil obtained in Example 1 were mixed to obtain the hypoglycemic composition.

Example 7

1 part by weight of the anise oil obtained in Example 1 and 20 parts by weight of the onion oil obtained in Example 1 were mixed to obtain the hypoglycemic composition.

Example 8 (I) Pharmacodynamic Experiment of the Hypoglycemic Composition Having Hypoglycemic Function 1. Experimental Objective To establish a rat model of hyperglycemia induced by dexamethasone, and to preliminarily explore the hypoglycemic effect on hyperglycemic rats.

2. Experimental Materials 2.1 Medicaments and Main Reagents
(1) Main Reagents
The hypoglycemic composition obtained in above Example 4 was used; glucose (AR grade), Shanghai fourth Reagent Factory; Dexamethasone Sodium phosphate Injection, Wuhan Binhu Double-crane Pharmaceutical Co., Ltd.
(2) Experimental Animals
SD rats, male, SPF grade, body weight (150±20) g, provided by Animal experiment center of Hubei University of Chinese Medicine.

(3) Main Instrument
flow cytometer, BD corporation, the USA; Blood glucose meter: Sure Step Plus System, Johnson Company; Microplate reader: Bio-Rad corporation, the USA; Model 722 Grating Spectrometer, Shanghai General Instrument Factory; Ultra low temperature freezer, Thermo Fisher Scientific the USA; Electronic analytical balance, BS124S, Startorius corporation, Germany; Ultra-pure water system, Mill-Q II, Milipore, Bedford, Mass., USA; Rat metabolic cage, Suzhou Fengshi Laboratory Animal Equipment Co., Ltd; Kit, Nanjing Jiancheng Bioengineering Institute.

3. Experimental Methods 3.1 Establishment of Models and Pharmacological Intervention The rats were reared in the SPF grade barrier animal laboratory in experimental animal center of Hubei University of Chinese Medicine. Daily care of animals and experimental conditions were in line with "the experimental animal environment and facilities standards, Ministry of health, People's Republic of China".

The rats were accommodated and reared for 3-5 days using ordinary maintenance feeds, fasted for 3-4 hours, and then tail blood was withdrawn. Fasting blood glucose values, i.e. the blood glucose values before the administration of glucose (0 hour) were measured, and the blood glucose values at 0.5 and 2 hours after the administration of 2.5 g/kg BW of glucose were measured, as the basal values of that batch of animals.

Establishment of models: the rats were divided into 5 groups based on blood glucose levels at 0 h, 0.5 h: blank control group, model control group and three sample groups with 15 rats in each group.

After rearing each group with maintenance feeds for 1 week, the feeds for model control group and the 3 sample groups were changed to high calorie feeds. After rearing for 2 weeks, the model control group and 3 sample groups, on the basis of high calorie feeds, were respectively given dexamethasone 0.8 mg/kg BW intraperitoneal injection (0.008% dexamethasone, injected amount: 1 ml/100 g body weight), once a day, for continuous 10 days.

Prophylactic administration: the blank control group was not treated, the 3 sample groups were intragastrically administrated with high, medium and low doses of hypoglycemic composition, the administered doses were respectively 17.5 mg/kg·d, 35.0 mg/kg·d, 70.0 mg/kg·d, the model control group was administered equal volume of pharmacological saline, for continuous 42 days.

3.2 Sample Collection and Indexes Detection
Fasting glucose and glucose tolerance (blood sample): after the completion of the experiments, animals in each group were fasted for 3-4 hours, and the blood from tail vein was used for the determination of fasting blood glucose; after 15-20 minutes, each group was administered with oral glucose 2.5 g/kg BW, and the blood from tail vein was respectively withdrawn at 0.5 h and 2 h for the determination of blood glucose tolerance.

Insulin, cholesterol, triglyceride, HbAlc levels (blood sample): After the completion of the glucose tolerance test, orbital venous blood was withdrawn, and the serum was separated and kept in a freezer at −80° C.

Hepatic glycogen, muscle glycogen, pancreatic islet B cell apoptosis rate (tissue): after glucose tolerance test was completed, the liver and pancreas were quickly removed, wherein the liver was washed with 0.15 MKCI-EDTA solution and then kept at −80° C., and the pancreatic islet B cell apoptosis rate was detected by flow cytometer.

Kits were used to respectively detect the biochemical indexes of each group, and the results were shown by mean+SD. SPSS statistical software (12.0) was used to subject the results to ANOVA analysis.

4. Experimental Results

After the completion of the experiments, the changes of levels of biochemical indexes of rats in each group were shown in Table 1-Table 3.

TABLE 1

Comparison of glucose tolerance in rats of different groups - Example 8

| Group | Number of cases | Fasting blood glucose (mmol/L) | Blood glucose after 0.5 h (mmol/L) | Blood glucose after 2 h (mmol/L) | AUC |
|---|---|---|---|---|---|
| blank group | 15 | 3.58 ± 0.05 | 5.48 ± 0.42 | 4.91 ± 0.33 | 640.4 ± 24.6 |
| model group | 15 | 4.24 ± 0.13## | 7.09 ± 0.29## | 6.88 ± 0.24## | 738.6 ± 46.5## |
| low dose group | 15 | 4.05 ± 0.67 | 6.08 ± 0.68 | 6.54 ± 0.11 | 723.64 ± 31.77 |
| medium dose group | 15 | 3.84 ± 0.01✕ | 5.67 ± 0.60✕ | 6.11 ± 0.14✕ | 720.81 ± 34.51 |
| high dose group | 15 | 3.79 ± 0.06✕ | 5.52 ± 0.12✕✕ | 6.07 ± 0.16✕ | 720.78 ± 41.82 |

Note:
compared with blank group $p < 0.05$,
compared with blank group $p < 0.01$,
✕compared with model group $p < 0.05$,
✕✕compared with model group group $p < 0.05$.

After rearing with high fat feeds, the levels of fasting blood glucose of the rats in the model group were significantly increased compared with the normal group ($P<0.05$); at 30, 120 minutes after glucose load, the blood glucose was significantly increased, and the difference from the blood glucose value of rats in the normal diet group at the same time point was statistically significant ($P<0.05$); at the same time, the area under the curve of glucose in model group was significantly higher than that of the normal group, and the difference was statistically significant ($P<0.05$).

By observing the fasting blood glucose, compared with the model group, low, medium and high dose groups were all decreased, but there were significant differences between medium and high dose groups and the model group ($P<0.05$); 0.5 h after glucose load, there was statistical significance in the differences between the medium and high dose groups of the sample groups and model group ($P<0.05$), but no significant difference between the groups ($P>0.05$); 2 h after glucose load, there was statistical significance in the differences between medium and high dose groups and model group ($P<0.05$); by observing the fasting blood glucose, the area under the curve at 0.5 h, 2 h after glucose load, there was no significant difference between high, medium and low dose groups and the model group ($P>0.05$), but there was significant difference compared with the normal group ($P<0.05$).

The rats in model group showed significant differences compared with those of blank group in terms of cholesterol, triglyceride, insulin, HbA1c ($P<0.05$), indicating that the establishment of models was successful.

As for cholesterol, there were always significant differences between rats in sample groups and in the model group ($P<0.05$); there was no significant difference between each sample group ($P>0.05$); as for triglycerides, there were always significant differences between rats in sample groups and in the model group ($P<0.05$); as for insulin, there were always significant differences between rats in each of the sample groups and in the model group ($P<0.05$); as for HbA1c, there were always significant differences between rats in sample groups and in the model group ($P<0.05$).

TABLE 3

Comparison of hepatic glycogen, muscle glycogen and pancreatic islet β cell apoptosis rate of rats in different groups - Example 8

| Group | Number of cases | muscle glycogen (mg/g) | hepatic glycogen (mg/g) | pancreatic islet β cell apoptosis rate (%) |
|---|---|---|---|---|
| blank group | 15 | 0.97 ± 0.11 | 15.01 ± 1.02 | 1.66 ± 0.09 |
| model group | 15 | 0.59 ± 0.05## | 7.12 ± 0.45## | 9.89 ± 0.11## |
| low dose group | 15 | 0.83 ± 0.10✕ | 11.09 ± 0.34✕ | 2.40 ± 0.42✕ |
| medium dose group | 15 | 0.93 ± 0.11✕ | 14.13 ± 0.05✕ | 1.88 ± 0.24✕ |

TABLE 2

Comparison of cholesterol, triglyceride, insulin and HbA1c in rats of different groups - Example 8

| Group | Number of cases | cholesterol (TC) | triglyceride (TG) | insulin (INS) | HbA1c (g/ml) |
|---|---|---|---|---|---|
| blank group | 15 | 0.96 ± 0.43 | 1.35 ± 0.31 | 24.92 ± 1.44 | 13.81 ± 1.64 |
| model group | 15 | 2.67 ± 0.32## | 3.52 ± 0.20## | 11.91 ± 1.66## | 30.35 ± 4.78## |
| low dose group | 15 | 1.89 ± 0.48 | 1.88 ± 0.15✕ | 18.89 ± 0.89✕✕ | 23.12 ± 4.22 |
| medium dose group | 15 | 1.56 ± 0.42✕ | 1.59 ± 0.09✕ | 22.22 ± 0.88✕✕ | 19.98 ± 1.86✕ |
| high dose group | 15 | 1.46 ± 0.27✕✕ | 1.48 ± 0.21✕ | 23.02 ± 0.95✕✕ | 18.98 ± 4.35✕ |

Note:
compared with blank group $p < 0.05$,
compared with blank group $p < 0.01$,
✕compared with model group $p < 0.05$,
✕✕compared with model group group $p < 0.05$.

TABLE 3-continued

Comparison of hepatic glycogen, muscle glycogen and pancreatic islet β cell apoptosis rate of rats in different groups - Example 8

| Group | Number of cases | muscle glycogen (mg/g) | hepatic glycogen (mg/g) | pancreatic islet β cell apoptosis rate (%) |
|---|---|---|---|---|
| high dose group | 15 | 0.96 ± 0.07✕ | 14.20 ± 1.41✕ | 1.92 ± 0.11✕ |

Note:
compared with blank group $p < 0.05$,
compared with blank group $p < 0.01$,
✕compared with model group $p < 0.05$,
✕✕compared with model group group $p < 0.05$.

The rats in model group showed significant differences compared with those of blank group in terms of hepatic glycogen, muscle glycogen, apoptotic number of pancreatic islet cells (P<0.05), indicating that the establishment of models was successful.

The rats in each of the sample groups showed significant differences compared with model group in terms of hepatic glycogen, muscle glycogen, pancreatic islet β cell apoptosis rate (P<0.05), and showed significantly increased muscle glycogen, hepatic glycogen and decreased pancreatic islet β cell apoptosis rate.

As for hepatic glycogen, there was no significant difference between each group of the sample groups (P>0.05).

5. Summary of the Experiments (1) Each dose group of the hypoglycemic composition has hypoglycemic effect on rats of hyperglycemia model induced by dexamethasone.

(2) After comparing the effects of each dose group, it was found that the medium and high dose groups showed better supporting hypoglycemic effect on rats with impaired glucose and lipid metabolism, and there was no significant difference between the groups.

Example 9

Referring to the animal experimental method in Example 8, the hypoglycemic compositions of Example 1 and Example 7 were respectively used in replacement of the hypoglycemic composition of Example 4 to conduct the experiments.

The administered doses of sample groups were all 35.0 mg/kg·d.

After the completion of the experiments, the changes of levels of biochemical indexes of rats in each group were shown in Table 4-Table 6.

TABLE 4

Comparison of glucose tolerance in rats with compositions of different ratios

| Group | Number of cases | Fasting blood glucose (mmol/L) | Blood glucose after 0.5 h (mmol/L) | Blood glucose after 2 h (mmol/L) | AUC |
|---|---|---|---|---|---|
| blank group | 15 | 3.58 ± 0.05 | 5.48 ± 0.42 | 4.91 ± 0.33 | 640.4 ± 24.6 |
| model group | 15 | 4.24 ± 0.13## | 7.09 ± 0.29## | 6.88 ± 0.24## | 738.6 ± 46.5## |
| Example 1 | 15 | 4.32 ± 0.44 | 5.83 ± 0.12✕ | 6.22 ± 0.79✕ | 723.64 ± 31.77 |
| Example 7 | 15 | 4.15 ± 0.44 | 5.91 ± 0.03✕ | 6.52 ± 0.29✕ | 730.64 ± 40.77 |

Note:
compared with blank group $p < 0.05$,
compared with blank group $p < 0.01$,
✕compared with model group $p < 0.05$,
✕✕compared with model group group $p < 0.01$.

By observing fasting blood glucose, there was no statistical significance in the differences between each sample group and the model group (P>0.05); 0.5 h after glucose load, there was always statistical significance in the differences between each sample group and the model group (P<0.05); 2 h after glucose load, there was always statistical significance in the differences between each sample group and the model group (P<0.05); by observing fasting blood glucose, the area under the curve at 0.5 h, 2 h after glucose load, there was no statistical significance in the differences between sample groups and model group (P>0.05).

TABLE 5

Comparison of cholesterol, triglyceride, insulin and HbAlc in rats of different groups

| Group | Number of cases | cholesterol (TC) (mmol/L) | triglyceride (TG) (mmol/L) | insulin (INS) (ng/mL) | HbAlc (g/ml) |
|---|---|---|---|---|---|
| blank group | 15 | 0.96 ± 0.43 | 1.35 ± 0.31 | 24.92 ± 1.44 | 13.81 ± 1.64 |
| model group | 15 | 2.67 ± 0.32## | 3.52 ± 0.20## | 11.91 ± 1.66## | 30.35 ± 4.78## |

TABLE 5-continued

Comparison of cholesterol, triglyceride, insulin and HbA1c in rats of different groups

| Group | Number of cases | cholesterol (TC) (mmol/L) | triglyceride (TG) (mmol/L) | insulin (INS) (ng/mL) | HbA1c (g/ml) |
|---|---|---|---|---|---|
| Example 1 | 15 | 1.80 ± 0.28✕ | 2.45 ± 0.12✕ | 19.72 ± 1.44✕ | 22.72 ± 3.89✕ |
| Example 7 | 15 | 1.91 ± 0.26✕ | 2.10 ± 0.13✕ | 18.29 ± 1.44✕ | 25.11 ± 4.64✕ |

Note:
compared with blank group $p < 0.05$,
compared with blank group $p < 0.01$,
✕compared with model group $p < 0.05$,
✕✕compared with model group group $p < 0.01$.

As for cholesterol, there were always significant differences between rats in each sample group and in the model group ($P<0.05$); as for triglycerides, there were significant differences between rats in each sample group and in the model group ($P<0.05$); as for insulin, there were always extraordinary significant differences between rats in each sample group and in the model group ($P<0.01$); as for HbA1c, there were always significant differences between rats in each sample group and in the model group ($P<0.05$).

TABLE 6

Comparison of hepatic glycogen, muscle glycogen and pancreatic islet β cell apoptosis rate of rats in different groups

| Group | Number of cases | muscle glycogen (mg/g) | hepatic glycogen (mg/g) | pancreatic islet β cell apoptosis rate (%) |
|---|---|---|---|---|
| blank group | 15 | 0.97 ± 0.11 | 15.01 ± 1.02 | 1.66 ± 0.09 |
| model group | 15 | 0.59 ± 0.05## | 7.12 ± 0.45## | 9.89 ± 0.11## |
| Example 1 | 15 | 0.80 ± 0.16✕ | 11.25 ± 0.55✕ | 2.00 ± 0.32✕✕ |
| Example 7 | 15 | 0.76 ± 0.11✕ | 11.25 ± 1.07✕ | 3.19 ± 0.66✕✕ |

Note:
compared with blank group $p < 0.05$,
compared with blank group $p < 0.01$,
✕compared with model group $p < 0.05$,
✕✕compared with model group group $p < 0.05$.

The muscle glycogen and hepatic glycogen were all significantly increased, and pancreatic islet β cell apoptosis rates were all decreased. As for hepatic glycogen, muscle glycogen, pancreatic islet β cell apoptosis rate, there was always significant differences between rats in each sample group and in model group ($P<0.05$).

Conclusion: the results indicated that anise oil and onion oil compositions with different ratios all showed significant hypoglycemic effect.

The above is only the preferred embodiments of the present invention. It should be pointed out that those having ordinary skill in the art can also make some improvements and adaptions without departing from the principle of the present invention, and the improvements and adaptions should be regarded as within the protection scope of the present invention.

What is claimed is:

1. A hypoglycemic composition, comprising: 1-99 parts by weight of anise oil and 1-99 parts by weight of onion oil, wherein the anise oil is obtained by subjecting anise to steam distillation, and the onion oil is obtained by subjecting onion to steam distillation.

2. The hypoglycemic composition according to claim 1, wherein the composition comprises 1-40 parts by weight of anise oil and 1-40 parts by weight of onion oil.

3. The hypoglycemic composition according to claim 1, wherein the composition comprises 1-20 parts by weight of anise oil and 1-20 parts by weight of onion oil.

4. The hypoglycemic composition according to claim 1, wherein the composition comprises 1-10 parts by weight of anise oil and 1-10 parts by weight of onion oil.

5. A method for preparing the hypoglycemic composition of claim 1, comprising:
   A) pulverizing anise and subjecting the resultant powder to steam distillation to obtain anise oil;
   B) pulverizing onion and subjecting the resultant powder to steam distillation to obtain onion oil; and
   C) mixing 1-99 parts by weight of anise oil and 1-99 parts by weight of onion oil to obtain the hypoglycemic composition.

6. The method according to claim 5, wherein step A) is performed by:
   pulverizing anise, then soaking the resultant in water, and then subjecting the resultant to distillation by heating to obtain anise oil;
   pulverizing onion, then soaking the resultant in water, and then subjecting the resultant to distillation by heating to obtain onion oil.

7. The method according to claim 6, wherein the anise is soaked in water for 10-30 h after being pulverized; the onion is soaked in water for 10-30 h after being pulverized.

8. A method for treating hyperglycemia in a subject in need thereof comprising administering to the subject the hypoglycemic composition according to claim 1.

9. A health food for treating hyperglycemia, comprising the hypoglycemic composition according to claim 1.

10. A method for treating hyperglycemia in a subject in need thereof comprising administering to the subject the hypoglycemic composition obtained by the method according to claim 5.

11. A health food for treating hyperglycemia, comprising the hypoglycemic composition obtained by the method according to claim 5.

* * * * *